(12) United States Patent
Stockwell et al.

(10) Patent No.: US 10,969,344 B2
(45) Date of Patent: Apr. 6, 2021

(54) DETECTING THE PRESENCE OF LIQUID IN A HIGH PRESSURE GAS PIPELINE

(71) Applicant: PROCESS VISION LIMITED, Basingstoke (GB)

(72) Inventors: Paul Stockwell, Baildon (GB); David Widdup, Baildon (GB); Jon Raynes, Baildon (GB)

(73) Assignee: Process Vision Limited

( * ) Notice: Subject to any disclaimer, the term of this patent is extended or adjusted under 35 U.S.C. 154(b) by 469 days.

(21) Appl. No.: 15/575,923

(22) PCT Filed: May 25, 2016

(86) PCT No.: PCT/GB2016/051507
§ 371 (c)(1),
(2) Date: Nov. 21, 2017

(87) PCT Pub. No.: WO2016/189300
PCT Pub. Date: Dec. 1, 2016

(65) Prior Publication Data
US 2018/0088054 A1  Mar. 29, 2018

(30) Foreign Application Priority Data
May 26, 2015 (GB) .................................. 1508948

(51) Int. Cl.
*G01P 3/36* (2006.01)
*G01N 21/85* (2006.01)
(Continued)

(52) U.S. Cl.
CPC ............. *G01N 21/85* (2013.01); *G01F 1/002* (2013.01); *G01F 1/661* (2013.01); *G01F 1/663* (2013.01);
(Continued)

(58) Field of Classification Search
CPC ...... G01N 33/225; G01N 21/85; G01F 22/00; G01F 1/74; G01F 1/661; G01F 1/663;
(Continued)

(56) References Cited

U.S. PATENT DOCUMENTS

| 9,611,735 B2 * | 4/2017 | Tjhang | G01N 21/51 |
| 2008/0180693 A1 * | 7/2008 | Dillon | G01B 11/2441 356/521 |

(Continued)

FOREIGN PATENT DOCUMENTS

| CN | 103424406 A | 12/2013 |
| GB | 2509716 A | 7/2014 |

(Continued)

OTHER PUBLICATIONS

Al Hsin Lee, et al., Study of Flow Regime Transitions of Oil-Water-Gas Mixtures in Horizontal Pipelines, Proceedings of the Third (1993) International Offshore and Polar Engineering Conference, Singapore, Jun. 6-11, 1993, XP055301273, Retrieved from the Internet: URL:http://www.icmt.ohio.edu/documents/publications/8006.pdf.

*Primary Examiner* — Mark Hellner
(74) *Attorney, Agent, or Firm* — GrayRobinson, P.A.; Michael J. Colitz, III (57) ABSTRACT

An apparatus for detecting the presence of liquid in a high pressure gas pipeline (4) is described. The apparatus comprises a sight glass (2), providing a window into the inside of the pipeline, and a light sensor (1), for receiving and sensing reflected light from the inside of the pipeline through the sight glass. The apparatus also comprises a processor, for automatically detecting the presence of a liquid based on the sensed reflected light. In this way, automatic detection of the presence of liquid in a gas pipeline can be achieved based on the measurement of reflected light, which can be expected to differ when liquid (Continued)

is present compared with when no liquid is present. No visual inspection by an operator is required—although the data can be stored for later operator use or verification if necessary.

50 Claims, 9 Drawing Sheets (51) Int. Cl.
*G01N 33/22* (2006.01)
*G01F 1/74* (2006.01)
*G01F 1/66* (2006.01)
*G01F 1/00* (2006.01)
*G01F 15/02* (2006.01)
*G01F 15/06* (2006.01)
*G01F 22/00* (2006.01)
*G01P 5/26* (2006.01)

(52) U.S. Cl.
CPC .............. *G01F 1/74* (2013.01); *G01F 15/022* (2013.01); *G01F 15/06* (2013.01); *G01F 22/00* (2013.01); *G01N 33/225* (2013.01); *G01P 5/26* (2013.01); *G01F 1/66* (2013.01)

(58) Field of Classification Search
CPC . G01F 1/002; G01F 1/66; G01F 15/06; G01F 15/022; G01P 5/26
USPC .......................................................... 356/28
See application file for complete search history.

(56) References Cited

U.S. PATENT DOCUMENTS

| | | | |
|---|---|---|---|
| 2013/0215411 A1* | 8/2013 | Christian | .................. G01P 5/26 356/28.5 |
| 2015/0216415 A1* | 8/2015 | Uribe-Patarroyo | ......................... A61B 5/0066 600/476 |
| 2015/0276589 A1* | 10/2015 | Wagner | .................. G01N 21/39 356/440 |

FOREIGN PATENT DOCUMENTS

| | | | |
|---|---|---|---|
| JP | S6379017 A | 4/1988 | |
| WO | 2011073789 A3 | 11/2011 | |
| WO | WO2015/024118 | * 2/2015 | .............. G01P 15/18 |

* cited by examiner

DETECTING THE PRESENCE OF LIQUID IN A HIGH PRESSURE GAS PIPELINE

CLAIM OF PRIORITY

This application is a continuation of and claims priority under 35 U.S.C. § 371 to International Application No. PCT/GB2016/051507 filed on May 25, 2016, which in turn claims priority to GB App. No. 1508948.5 filed on May 26, 2015, the contents of which are incorporated herein by reference for all purposes.

FIELD OF THE INVENTION

The present invention relates to an apparatus and method for detecting the presence of liquid in a high pressure gas pipeline using optical techniques with sight glass or glasses apparatus.

BACKGROUND TO THE INVENTION

High pressure gas pipelines are used to transport natural gas. Sometimes, liquid may be present in the gas volume, and may be conveyed along the pipeline along with the gas. Generally, the presence of liquid in a gas pipeline is undesirable, and it is therefore beneficial to be able to detect its presence, and preferably to monitor how much liquid is present in the pipeline (volume) and the flow rate of liquid through the pipeline (volumetric flow rate). The determination of low levels of liquid has been attempted before but poses particular problems for many systems using techniques such as sonic and ultrasonic, microwave, time of flight distance measurement systems and laser triangulation.

Detection of liquids in a pipeline can have complex requirements to characterise both high speed and low speed particles and liquid flows. It follows that a variety of techniques are required to fully characterise the liquid flow when present. For example, optical systems in high pressure gas systems need to have the primary optical component (sight glass or sight glasses) in contact with high pressure in the pipeline. Two problems exist with optical components in gas pipe lines that have been addressed in the Applicant's previous patent applications. In particular, these detail a sight glass with secondary containment, and a triangulation system to determine liquid depth on the pipe wall. While this works well in high pressure vessels and low velocity gas flows in pipelines, when liquid is present in high velocity gas flows, droplets of liquid are picked up by the gas and thrown forward making a laser based triangulation or optical distance measurement system using time of flight system susceptible to high levels of noise as droplets pass through the field of view. The presence of aerosols in the gas flow similarly results in high noise levels.

Some pipeline inspection systems use an imaging system in a pipeline, mounted on pigs or small vehicles to inspect the internal pipe wall for defective welds, corrosion and other defects in the pipe.

Embodiments of the present invention seek to address some of the problems associated with detecting liquid in gas pipelines.

SUMMARY OF THE INVENTION

According to an aspect of the present invention, there is provided an apparatus for detecting the presence of liquid in a high pressure gas pipeline, comprising:

a sight glass or sight glasses, providing an aperture into the inside of the pipeline;
one or more light sources
a light sensor, for receiving and sensing reflected light from the inside of the pipeline through the sight glass; and
a processor, for automatically detecting the presence of a liquid based on the sensed reflected light.

In this way, automatic detection of the presence of liquid in a gas pipeline can be achieved based on the measurement of reflected light, which can be expected to differ when liquid is present compared with when no liquid is present. No visual inspection by an operator is required—although any relevant process data that may be required by the user can be stored for later operator use or live verification if necessary. This system therefore is able to determine liquid flow at low liquid levels in high pressure gas flows within a pipeline.

In some embodiments, different flow regimes for the liquid within the pipeline can be automatically detected. None of the techniques previously proposed are able to recognise different flow regimes at low liquid levels. It is believed that using a visual imaging technique works better than other techniques at low Liquid Volume Fractions (LVF), as this is where other techniques such as ultrasonic or microwave require very high sensitivity.

Generally, the present technique relates to gas pipelines at high pressures that have a 90% Gas Volume Fraction (GVF), or higher, and the Liquid Volume Fraction (LVF) is 10%, or lower. When gas flows in a pipeline, it is usually induced by a pressure differential between the entry point and the exit point of the pipe system. The determination of liquid present in wet gas flow in gas pipelines presents specific problems. When low levels of liquid are entrained in the gas flow, a high percentage of that liquid hits the pipe wall and remains on the wall. It moves along the pipe wall and a flow is induced due to friction with the gas phase. In horizontal pipelines, at low liquid flow levels, the liquid usually forms a film on the pipe wall that sinks (under gravity) to the floor of the pipe. In smaller diameter pipes, and at higher pressures, where there is sufficient energy in the gas flow, the film may form an annular flow around the full circumference of the pipe. In larger diameter pipes, or at lower flow rates, the film may sink to the bottom of the pipe and form a slow moving stable stream (smooth stratified flow). If the liquid content increases the stream may start "wavy flow": when the depth of the liquid at the bottom of the pipe is sufficient, rapidly moving waves on the surface of the stream appear. If the liquid flow increases further, "slugged flow" and then "bubble flow" regimes commence.

There are complex flow regimes and patterns that vary due to many different factors, for example: liquid flow rate, gas flow rate, gas pressure, gas density, liquid density, liquid viscosity, pipe diameter and temperature. At low liquid flow levels, there is a big difference between the velocity of the gas and the velocity of the liquid film or stream on the pipe wall.

Any system to detect and measure these flows needs to be very sensitive. The presence of droplets and aerosols also present in the pipeline, and traveling at high speed, can cause noise in flow or liquid depth measurement systems.

The present device and method monitors liquid flows and automatically determines the onset of different liquid flow regimes at low liquid flow levels in high pressure pipe systems. These pipelines can range in diameter from 2" to 48" and larger.

The data produced by our device can be used to determine volumetric liquid flow, and can also be used by a flow computing system to improve the accuracy of other gas flow measurement devices.

The device can also determine the size, volume and velocity of liquid droplets entrained in the gas flow, and of smaller aerosols enabling an estimate of total liquid flow to be made in wet gas systems. The device may be used to alert operators of liquid carry-over in a normally dry gas flow from, for example, a gas/liquid separator, or to characterise and measure fluids in a wet gas flow.

A system to detect and characterise liquid flows in pipelines at low liquid content and wet gas flows using an illumination, imaging or light detection system, liquid flows within a high pressure pipe can be determined. The volume of liquid and the velocities of the liquid surface can be measured. By measuring velocities and dimensions of the liquid stream to characterise the liquid present at the pipe wall or entrained in the gas flow and in aerosol form a calculation of total liquid flow may be made. An estimate of a three dimensional liquid flow on the pipe wall can also be established using algorithms to compute the total flow based on velocities on the surface of the liquid on the pipe floor.

Embodiments of the present invention may be particularly beneficial where the pipe or vessel contains high pressure combustible gas and/or a natural gas, making more invasive techniques hazardous and thus non-viable.

DETAILED DESCRIPTION

The invention will now be described by way of example with reference to the following Figures in which.

Figure 1:
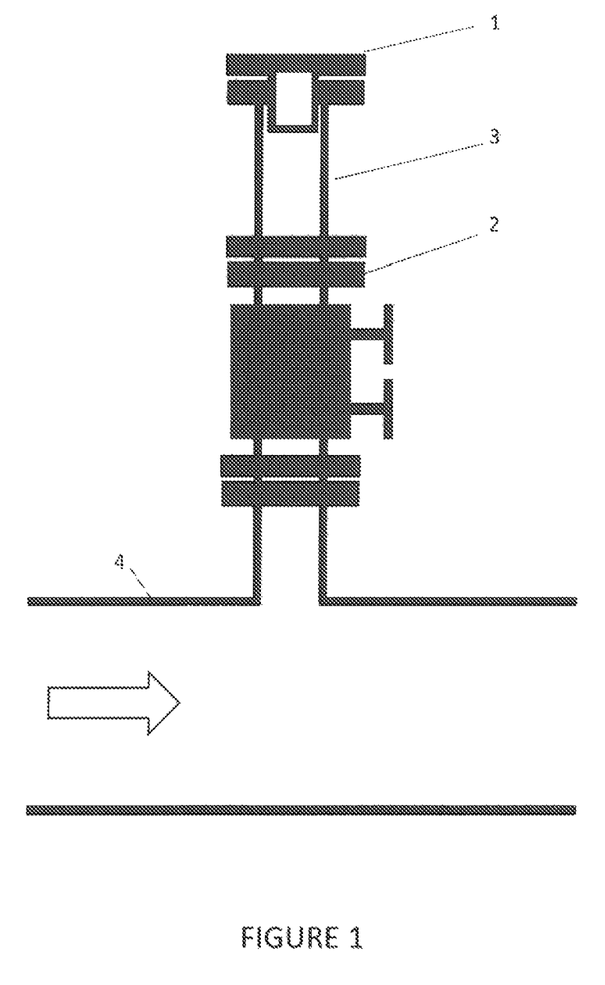
FIG. 1 schematically illustrates a liquid detection system mounted to a side pipe which branches perpendicularly from a horizontal gas pipeline.
Figure 2:
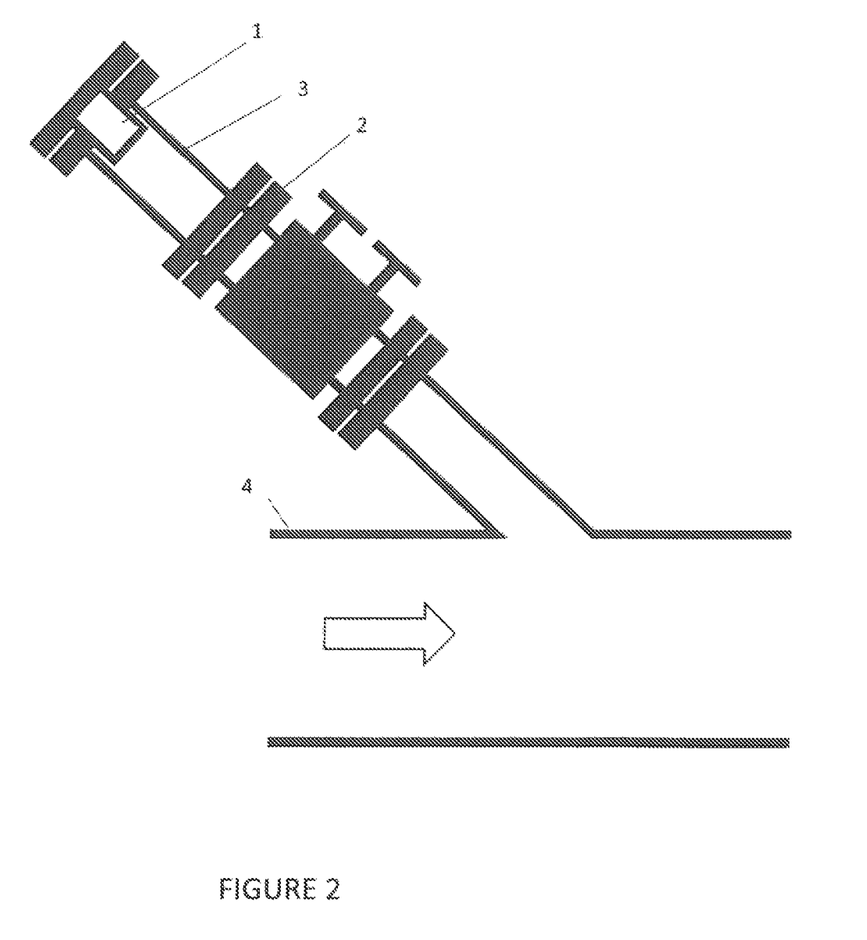
FIG. 2 schematically illustrates a liquid detection system mounted to a side pipe which branches at an angle from a horizontal gas pipeline.
Figure 3:
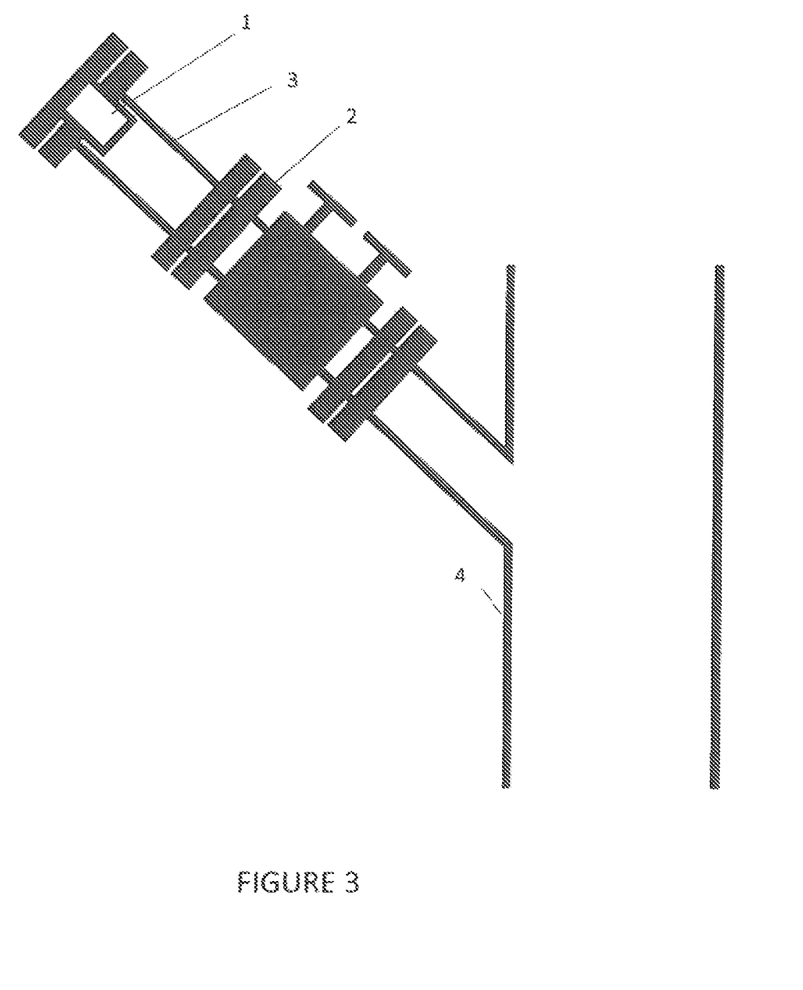
FIG. 3 schematically illustrates a liquid detection system mounted to a side pipe which branches at an angle from a vertical gas pipeline.

Referring first to FIG. 1, this shows an example of an optical system 1 mounted behind a sight glass or glasses 2 at a sufficient distance (0.2 metres or above) from the main flow in a pipeline 4 to enable the sight glass to remain largely free of contamination that may be present in the main fluid flow. The sight glass is used to provide a window into the inside of the pipeline, which is typically at a high pressure. The optical system 1 views the inside of the gas pipeline through this window. In particular, the sight glass 2 is provided at an end of a side pipe 3, which branches off of the main pipeline 4. In a horizontal pipe system the side pipe would typically be above the main pipe, either directly above or angled upwards from the main pipe. However, in principle the side pipe could be provided to one side or other of the main pipe, or even beneath it—although such implementations may suffer from increased contamination of the sight glass with liquids, due to the influence of gravity on liquids being conveyed along the main pipe. The optical system 1 may also be mounted at an angle to the main pipe 4 (for example, the side pipe could be at an angle, for example of 30° or 45° to the main pipeline), as shown in FIG. 2, thereby giving a greater field of view to the optical system. In particular, it can be seen that the field of view FOV2 in FIG. 2 is greater than the field of view FOV1 in FIG. 1. In this context, it will be appreciated that the term "field of view" is intended to indicate the (size of the) portion of the pipeline which the optical device is able to see. As a result of a larger field of view, the optical system is able to operate on a larger "sample" of information. On the other hand, the FIG. 2 embodiment would require more complex image processing in order to compensate for the geometric distortion of the image resulting from the angle, and additionally, the amount of light reflected back from the inside of the gas pipeline (from a light source provided as part of the optical system 1) is likely to be lower where that light is striking the inside of the pipeline/liquid surface at an angle, rather than striking perpendicularly. Preferably, as shown by the directional arrow in FIG. 2, the side pipe 3 projects backwards from the direction of fluid flow in the main pipe, to avoid (or at least reduce the likelihood of) liquid in the flow being driven up the side pipe 3. FIG. 3 shows a vertical pipe system comprising the main pipe 4, the optical system 1, the sight glass 2 and the side pipe 3. As with FIG. 2, the side pipe could be at an angle, for example of 30° or 45° to the main pipeline, or could be perpendicular as shown in FIG. 1. Gas flow in a vertical pipeline could be in either direction.

Optical System

In the simplest case, a simple light source might project light down the side pipe 3 and into the main pipe 4, while a simple photodetector detects the level of reflected light. In the case that no liquid is carried down the pipe, the level of reflected light can be expected to be relatively consistent. In the case that liquid is being conveyed down the pipe and past the mouth of the side pipe, the level of reflected light can be expected to vary more (due to the "shimmering" effect typically achieved when light is projected onto moving liquid). The amount of variance may therefore be indicative that liquid is present or of the amount of liquid present in the pipe. Should the variance exceed a threshold value, it may be determined that liquid is present in the gas pipeline or too much liquid is present in the gas pipeline. It may be possible, to a limited degree, to determine the likely flow regime based on the variance of the light level received at the photodetector. Moreover, typically (but not always) the presence of liquid is likely to change the average level of reflected light. For example, depending on the reflective properties of the liquid compared with that of the inside wall of the pipeline. Similarly therefore, the light level itself (averaged over a number of samples) may be used as the indicator of the presence of liquid, and where automatic detection of liquid is required the light level may be compared with a threshold to determine when too much liquid is present in the gas pipeline.

However, it is possible to provide a much more reliable estimate of liquid flow within the gas pipeline if an imaging device, such as a camera is used instead or as well as a simple photodetector. Image processing techniques can be used both to detect the liquid flow regime within the pipeline, and also to generate an estimate of liquid volume and volumetric flow rate within the pipeline, the calculation of which may be influenced by the flow regime. Furthermore, improved operation (either in the context of a photodetector or an imaging device) can be achieved by using a more advanced light source, as will be described below.

The optical system 1 comprises an illumination system that can be monochromatic or operate at multiple wavelengths including visible, IR, UV and terahertz frequencies depending on the nature of the fluid being monitored and the behaviour of the fluid being measured. If the receiving optical systems are able to filter out particular wavelengths, operation of multiple light sources operating at different wavelengths allows a variety of techniques to be used at the same time to allow different aspects of flow regimes to be highlighted and measured. In addition to wavelengths, the illumination sources may produce one beam, or a combination of shaped and focused beams such as spots, lines, grids or other patterns in order to aid the identification and measurement of different flow regimes. In particular, by projecting a pattern of illumination into the gas pipeline, this pattern may be distorted by the presence of liquid within the gas pipeline, and this distortion can be detected in the captured image (by comparing the position of the pattern of illumination in the captured image with its expected position when the pipeline is absent of any liquid) and used to infer the presence of liquid, and the flow type. For example, the inside wall of the gas pipeline will generally be curved, while a stream of liquid running along the bottom of the gas pipeline can be expected to have a relatively flat surface at low liquid flow speeds. The flat surface of such a stream can be detected based on distortion of the pattern of illumination.

Figure 13:
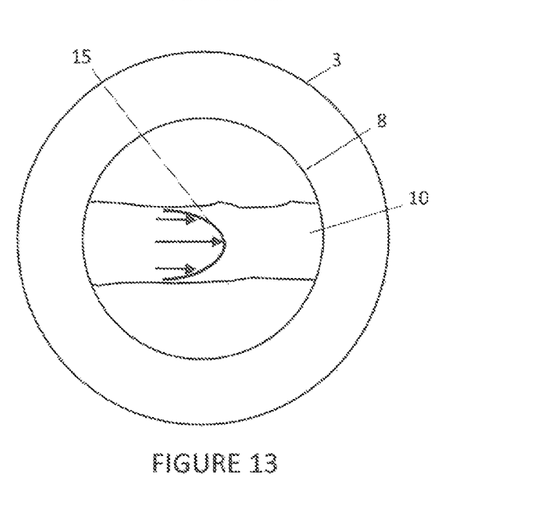
FIG. 13 schematically illustrates an example image of flow distribution across the width of a smooth stratified flow and FIG. 14 schematically illustrates the liquid detection system.

The use of collimated and uncollimated light can help distinguish features in the liquid stream. Uncollimated light may be used to determine the edges of the stream, possibly with the use of collimated light to determine the velocity or relative velocities of the liquid across the width of the liquid stream. Doppler speckle contrast imaging is a technique which may be used in this process. The determination of the velocity profile across the flow leads to a more accurate determination of flow volume and, as the liquid only moves under the influence of the gas, the liquid-gas fraction may be determined from the liquid velocity data. The relative determination of velocities is illustrated in FIG. 13, with the measurement of fluid velocities 15 across the liquid stream 10.

Figure 4:
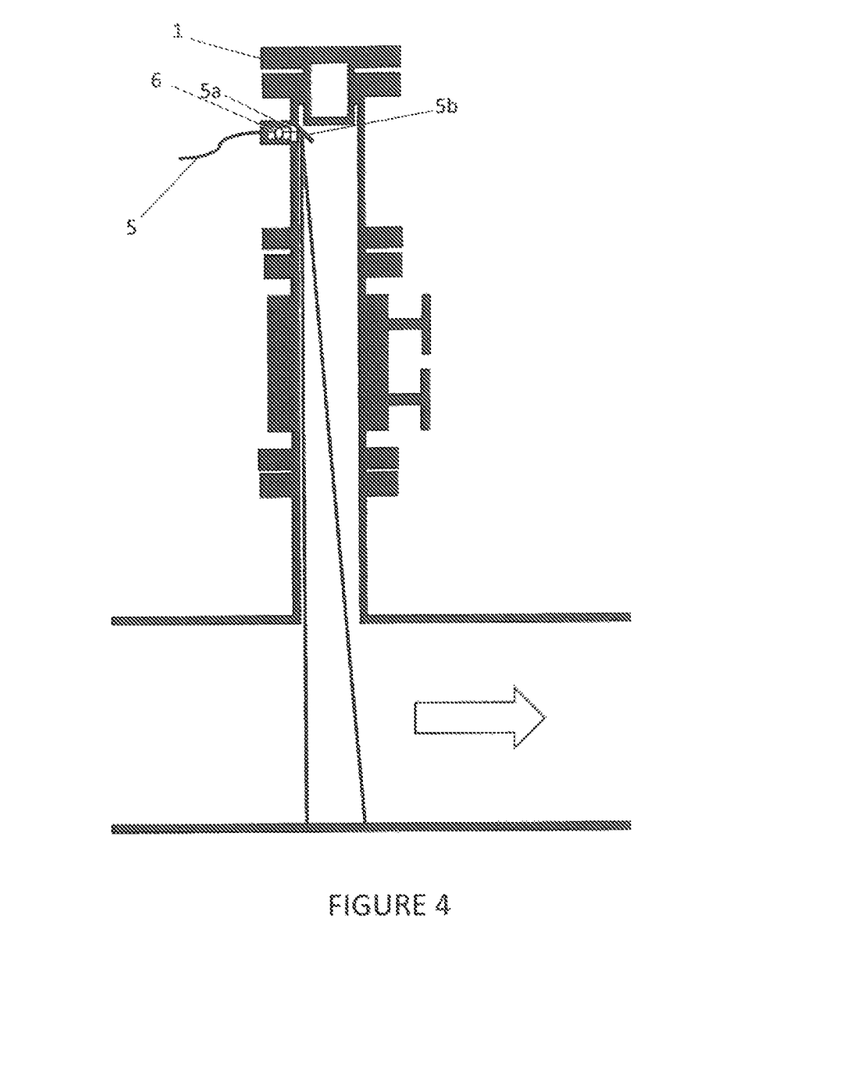
FIG. 4 schematically illustrates a liquid detection system using a light source which is offset from a light detection axis.

While the illumination source can be in line with a camera, some advantage can be gained by offsetting an illumination source 5, here a fibre optic, a lens 6 and a mirror 5b from the optical system 1, as shown in FIG. 4, thus creating shadows and better contrast on flowing liquids. The illumination source 5 may also be protected by a containment barrier 5a. The use of polarised light and polarising filters can determine the presence of liquids as the light reflected from the surface of a liquid will change its polar properties. When the polarising filter is at the correct angle to the incoming light only light reflected from the liquid can be observed, and reduce reflections that may interfere with image analysis when used with one or more cameras or imaging systems.

The use of a liquid or membrane type lens may be preferable in the optical system. The use of a, liquid or membrane lens offers many advantages in terms of their small size, reliability and safe operation in high risk areas. In addition, it may be used to change the focal length of the lens over short timescales and thus the rapid generation of depth of focus scans. In such an embodiment, the liquid or membrane type lens may be used to determine and classify aerosol volume at positions across the diameter of the pipeline to provide a fuller picture of the distribution of aerosol particles.

Figure 5:
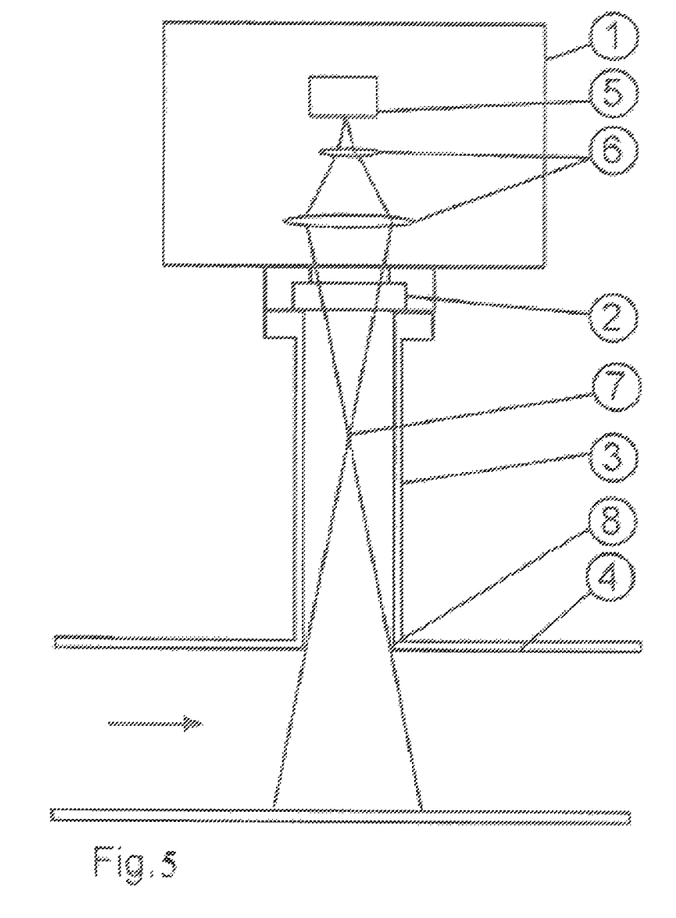
FIG. 5 schematically illustrates a liquid detection system having an illumination arrangement which projects light into an area outside of the field of view of the light detector, in order to detect aerosols or heat haze present in the gas pipeline.
Figure 6:
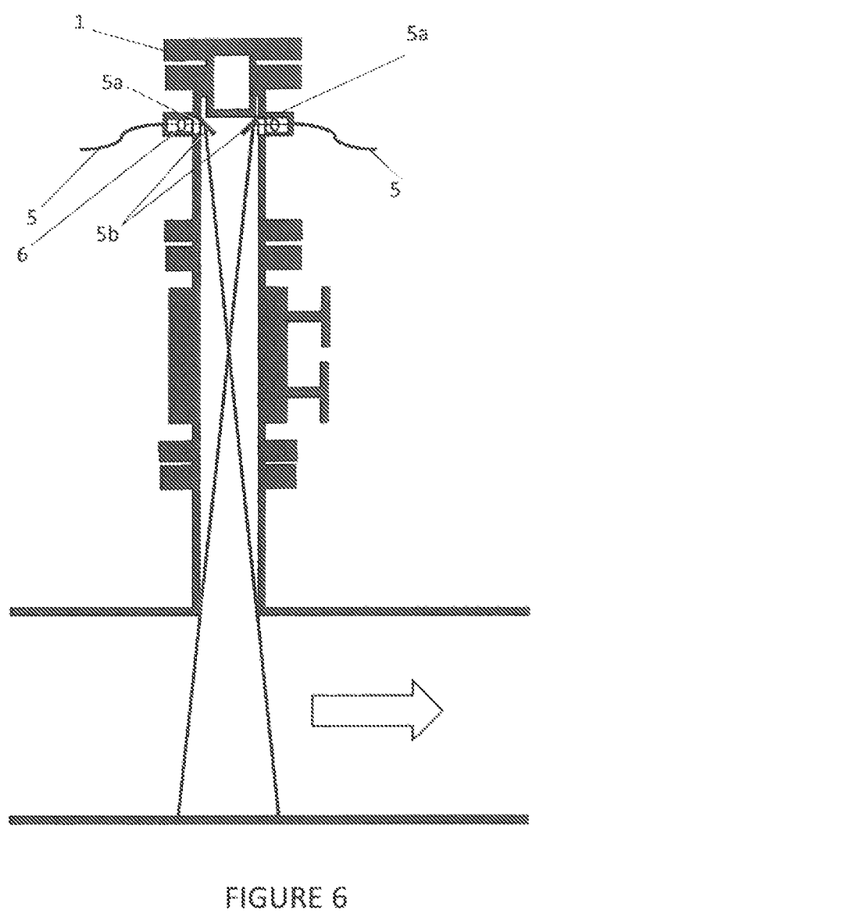
FIG. 6 schematically illustrates the use of multiple light sources to project light outside of the field of view of the light detector.

The illumination system 5 may also be employed to highlight aerosols and droplets suspended in the gas flow. This may be achieved by projecting and focusing a ring or lines outside the field of view (from the viewing point) when viewed from directly above. This has the advantage of avoiding light reflected from liquid on the pipe wall interfering with light reflected from droplets and aerosols. FIG. 5 illustrates a light ring set-up with an illumination source 5, and lenses or similar 6 focusing a ring of light to a point 7 within the vertical section of the system 3, so that the light ring is projected onto the pipe floor outside of the field of view when viewed from above. Mirrors, beam splitters and other optical components may be used to fold or combine the light path as may be required when mounting other optical components. FIG. 6 illustrates an alternative where two (or more) light sources may be used to project spots, lines or other shapes so that they are projected outside of the field of view of the imaging device. As mentioned above, an expected pattern of illumination can be distorted by a stream of liquid (flattened area), bumps in the stream (pulses of liquid/raised or wider areas of the stream), annular shape etc.

When the gas speed is high, for example 10 metres per second this is equal to 10 millimetres per millisecond therefore in order to get sharp images of droplets and particles at high speed, the camera must operate at high speed frame rates with continuous light. This produces large quantities of images for analysis. An alternative, and preferable system, is to operate the camera at slower frame rates, and have the illumination system modulate (or flash) at high speed (multiple times) within each frame. The illumination system may be set to flash just once per frame. However, when the illumination flashes twice or three times within one frame, each frame can be analysed to determine the velocity of particles and droplets within the frame and from frame to frame. In particular, if the illumination system flashes multiple times within a frame, a particular droplet (for example) may appear multiple times within a frame, as it passes across the field of view of the imaging device. The distance between each instance of the droplet within the frame is indicative of the velocity of that droplet.

The gas and liquids on the pipe wall are travelling at very different velocities and the use of multiple illumination and image capturing systems allows this system to determine both high speed particles suspended in the gas phase and slow liquids and particles moving on the pipe wall or on the surface of the liquid stream.

Imaging System

The optical system is designed to build an image of the full available field of view of the main pipeline 4 so that image analysis can determine the characteristics of the total liquid flow. Image processing may be used to determine the dimension of fixed points in the image (for example the mouth of the sidepipe) to enable a ratio measurement of other items of interest in the image. If a liquid is present, image processing can be used to determine which of the following liquid flow types exists when the gas flow rate is higher than the liquid flow.

Different flow regimes can be distinguished using image processing techniques. The main flow regimes considered are distributed flow, beaded flow, smooth stratified flow, wavy stratified flow, annular flow (full or partial), slugged flow, and bubble flow. Each of these flow regimes is described below in terms of it characteristics. Additionally, the image characteristics which can be used to identify and distinguish between these different flow regimes are also described.

Distributed Flow

Figure 7:
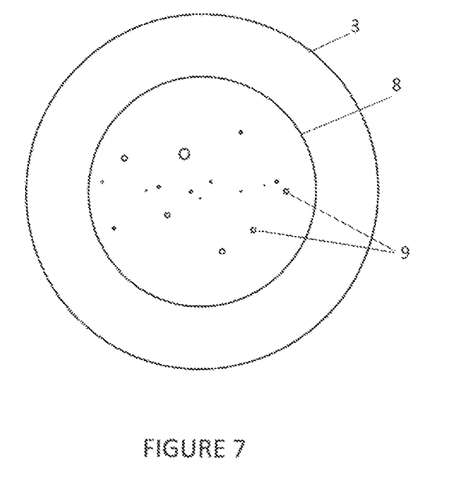
FIG. 7 schematically illustrates an example image of a distributed flow regime.

Extremely low liquid flow rates produce droplets borne along by the gas flow landing on the pipe wall. These droplets can be observed by an imaging system. FIG. 7 illustrates an image taken down the vertical section 3 of distributed flow of liquid droplets. The diameter of the lower limit of the vertical section 8 will be known and may be used as a fixed reference. In a well illuminated imaging system, the appearance of droplets can be highlighted by a computer based image processing system to recognise that a distributed flow is present, which can then activate a measurement system to determine the diameter of each of the droplets. Total liquid area and volume may be estimated to calculate liquid hold up. The rate at which droplet size and number increase (or decrease) over time can be estimated (as an indicator of liquid flow rate) and reported.

Beaded Flow

Figure 8:
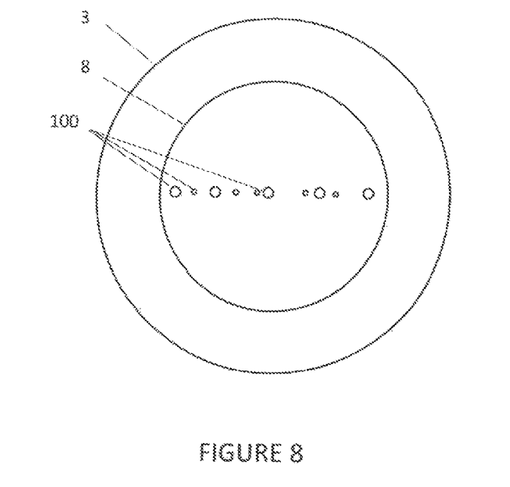
FIG. 8 schematically illustrates an example image of a beaded flow regime.

In the distributed flow (see FIG. 8), the droplets are static and separate. In contrast, in a beaded flow individual droplets 100 tend to conglomerate together and move along the pipe wall in the direction of gas flow (and under the influence of the gas flow). Again, liquid flow levels for a beaded flow are very low. As with the distributed flow, the diameter of each of the droplets can be evaluated, and the total liquid area and volume at a given time may be estimated. The rate at which the droplets move along the pipe wall can also be used to estimate the liquid flow rate. It will be appreciated that a flow regime may be a combination of distributed flow and beaded flow—i.e. that some droplets appear on the wall as per the distributed flow, while other droplets conglomerate together and/or move along the wall. In this case, the liquid volumes and flow rates can be determined from a combination of the rate at which droplet size and number increase, and the rate at which droplets are moving along the pipe wall.

Smooth Stratified Flow

Figure 9:
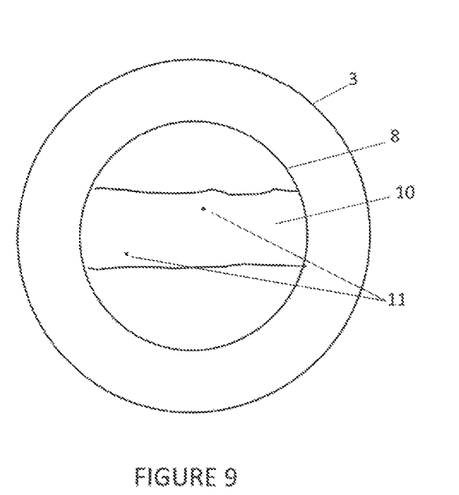
FIG. 9 schematically illustrates an example image of a smooth stratified flow regime.

Here, a stable stream of liquid is present at the pipe floor with little turbulence at the surface. In this regime there is a big difference or "slip" between the gas and liquid flows. FIG. 9 illustrates a smooth stratified flow. An image processing system is able to distinguish the edges of the stream, by the contrast between the liquid and the pipe wall. The image processing system is able to identify the average width of the stream, for example using the fixed points (e.g. the mouth of the side pipe 3) as a reference. When the main pipe 4 diameter is known, the liquid stream depth and area may be calculated from the width measurement to estimate liquid hold up. When bubbles or particles are observed on the surface of the liquid flow, their velocity may be determined by image analysis of either multiple frames or within one frame if the illumination system is modulated at a frequency higher than the frame rate. Alternatively, when a laser is used to illuminate, doppler speckle contrast may be used to determine the flow rates of the liquid passing through the field of view. A flow profile across the surface of the liquid stream may be determined where fluids in the middle of the stream are moving faster than those at the edges. Once calculated, the two dimensional flow profile may be applied to the three dimensional flow of the liquid stream on the pipe floor, and the total liquid flow rate of the stream can be estimated.

For smooth stratified flows, the width of the flow stream can be established by referencing known fixed points in the image (for example the diameter of the vertical pipe) against the width of the stream and applying geometry from the known diameter of the pipe. Once the width has been established, the depth and area can be calculated to determine the liquid hold up, or volume of liquid compared to the volume of gas.

In addition, the flow distribution across the surface of the stream can be determined by analysis of the particle position shift between modulations of the illumination, or between frames.

Once the surface velocity profile has been established, it can be applied to the three dimensional flow to estimate the total volumetric flow of the liquid stream. This has the advantage of using a real flow profile that will change with gas flow rate, liquid density and liquid viscosity.

Wavy Stratified Flow

Figure 10:
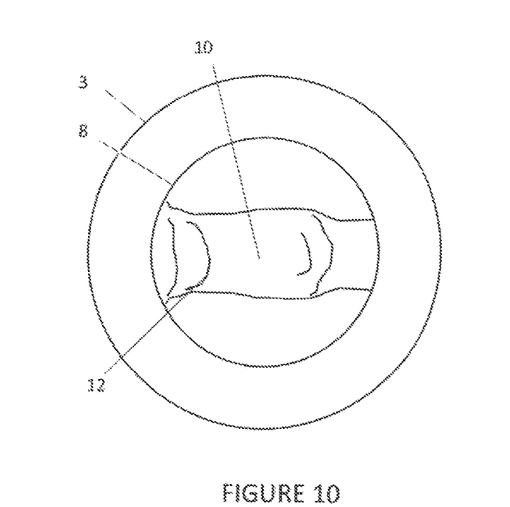
FIG. 10 schematically illustrates an example image of a wavy stratified flow regime.

When the depth of the liquid on the pipe floor and the friction with the gas is sufficient, pulses or waves move at high speed along the liquid stream on the pipe floor. FIG. 10 illustrates a wavy flow regime. A pulse 12 of liquid travels on the surface of the liquid stream temporarily increasing the width (and depth) of the liquid stream. Once recognised by the imaging system, the pulse size, frequency and duration can be used in addition to the width measurement to determine liquid hold up and liquid flow.

Figure 11:
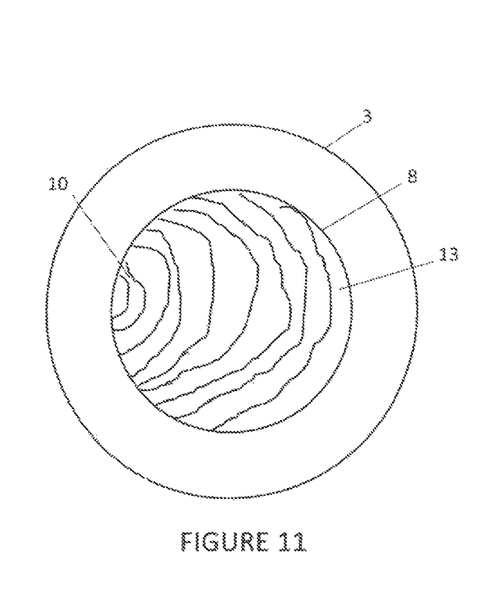
FIG. 11 schematically illustrates an example image of a part-annular flow regime.

Annular Flow

Where sufficient liquid is flowing, and there is sufficient energy in the gas flow, the liquid may be held up on the pipe wall, as shown in FIG. 11. In this case, the edges of the stream are outside of the field of view of the imaging device, and so cannot be observed and used to determine liquid volume and flow rate. However, the visible portion of the flow profile (difference in liquid flow speed across the width of the stream) can be used to estimate the width of the stream, or to directly estimate the liquid volume and flow rate. The flow profile can be used to determine a change in depth across the width of the stream. While these flows may exceed the field of view, the depth may be determined by the measurement of the flow profile at the bottom, and one or more other points in the field of view.

A short range scanning LIDAR system can be used to determine the depth of the liquid across the field of view. Here, a coherent illumination source at an angle to the liquid stream may project a line on to the bottom of the pipeline. As liquid enters the pipeline, the movement of said line can be used to determine the depth of the liquid stream. Such techniques are often inaccurate at pressure due to changes in the refractive index of the gas above the liquid flow. However, by scanning across the field of view, fixed reference points may be used to compensate for this issue as well as measurement drift and the presence of any 'heat haze', mirage or other refractive effect.

Alternatively high frequency ripples on the surface of the liquid, can be identified and used by the image processing system to help determine the flow regime type and the flow rates across the field of view.

Full Annular Flow

Figure 12:
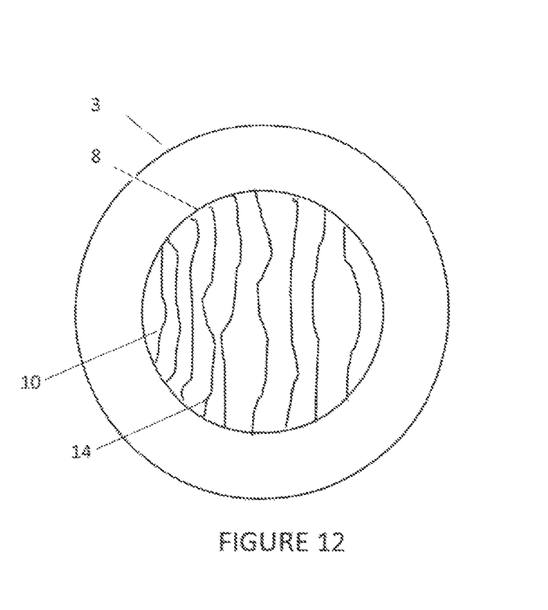
FIG. 12 schematically illustrates an example image of a full-annular flow regime.

In smaller diameter pipes there may be sufficient energy in the gas, and sufficient liquid present, to coat the full diameter of the pipe wall. An example of the liquid surface visible in such a regime can be seen in FIG. 12. Lower density liquid may tend towards a full annular flow. This can be determined by the different flow profile within the field of view. In particular, for a part-annular flow the variation in the liquid flow velocity across the captured image will be greater than for a full annular flow. Doppler speckle contract and short range scanning LIDAR may be used to determine or help determine the regime and flow rates. This can be appreciated from a comparison of FIGS. 11 and 12.

Slugged Flow

At higher liquid flows, the waves in the liquid stream are high enough to cover the full diameter of the pipe, and therefore are pushed down the pipe at high velocity. These can be determined by liquid rising up the vertical section when a slug passes through. This is clearly visible in a captured image. This feature can be automatically detected in a number of ways. For example, upon the liquid rising up the vertical section, the distinct edges of the mouth of the side pipe 3 will become indistinct. Alternatively, a pattern of illumination projected into the gas pipeline will be distorted substantially each time water rises up the vertical section.

Bubble Flow

At even higher liquid flows, the gas phase becomes bubbles within the liquid. With transparent liquids it is possible to estimate the gas volume by analysis of the images. With the flow regimes above, it is possible to analyse sequential images or frames where the illumination time is known and controlled, and the velocity of the liquid may be determined at multiple points across the width of the stream. At higher liquid flow levels the velocity of the bubbles may also be determined to indicate and identify the flow regime and flow rate.

Aerosol

If part of the illumination system, operating at a different wavelength, is arranged so that a shaped beam projects on to the pipe floor outside of the field of view, or area of interest, it removes the possibility that light reflected from the floor (or liquids at the pipe floor) would interfere with the power of reflected light and measurement made of from the aerosol in the gas stream. This will allow the determination of whether the gas is saturated with respect to either water vapour or hydrocarbon, and therefore is at (or higher than) its dew point temperature; an indication of aerosol content in the gas stream can also be calculated. Said aerosols may be liquids, solids or hydrates. Additionally, a LIDAR system may be used to measure the aerosol content of the pipe. Such a LIDAR system may use at least one liquid or membrane lens, due to the fast focusing properties of such a lens. A second liquid lens may be mounted on a camera to allow for rapid depth of field scans.

Heat Haze

High pressure gas pipe-lines, by definition, have higher density gases than those at atmospheric pressure. Density changes due to temperature are more significant at high pressure, and heat haze occurs at lower temperature differences than at atmospheric pressure. By imaging a full field of view that includes fixed item such as item 8 in FIG. 4 heat haze can be recognised and corrected for in image processing. This is because the fixed items will appear to move due to the presence of heat haze, and the occurrence of this, and the amount of movement, can be used to identify the presence of heat haze, and to determine the amount of distortion being caused by that heat haze. When the light source is a shaped spot, line or lines, grids or a matrix of spots, this also may assist in the recognition, measurement and correction of heat haze effects on the collected images. This is because projected spot, line, grid, or matrix will be distorted (displaced) from their expected position within an image frame, indicating the presence of heat haze. Moreover, the amount of distortion indicates an amount of heat haze. Based on the detection of heat haze, the image processing algorithms can be adapted to compensate for the heat haze. For example, if a pattern of spots, lines or grids is distorted with respect to its expected shape, an inverse geometric distortion can be applied to the image to compensate.

While one camera is envisaged for most measurements, image comparison or subtraction may be achieved by either changing illumination techniques between frames or when more than one camera is used with, for example, a polarised light system.

Image analysis may be achieved in a real time, or near to real time, system in order to produce alarms and measurements of liquids. Alternatively, images may be analysed later when the data is saved.

Metadata

Images of pipeline activity within a high pressure gas pipeline may be transmitted to operators live, or saved to allow examination at a later date. The images may be overlaid, or associated, with other data. Process and other data may be added to the images to enable them to be used as evidence of a particular pipeline at a particular time or date. Time, date, location, temperature, pressure gas flow, liquid flow and other relevant data could be added to the image during processing to allow easy viewing by engineers or other relevant people to provide data for process control decisions or evidence of inappropriate liquid flow. In the gas industry, a buyer of gas may wish to be able to reject gas the nature of which is unacceptable. For example, if the buyer is paying for a supply of dry natural gas, then the presence of substantial quantities of liquid within the gas supply pipeline may be unacceptable, and grounds for rejection of the delivery, or compensation. By storing or associating metadata with images, evidence is available in support of this.

Figure 14:
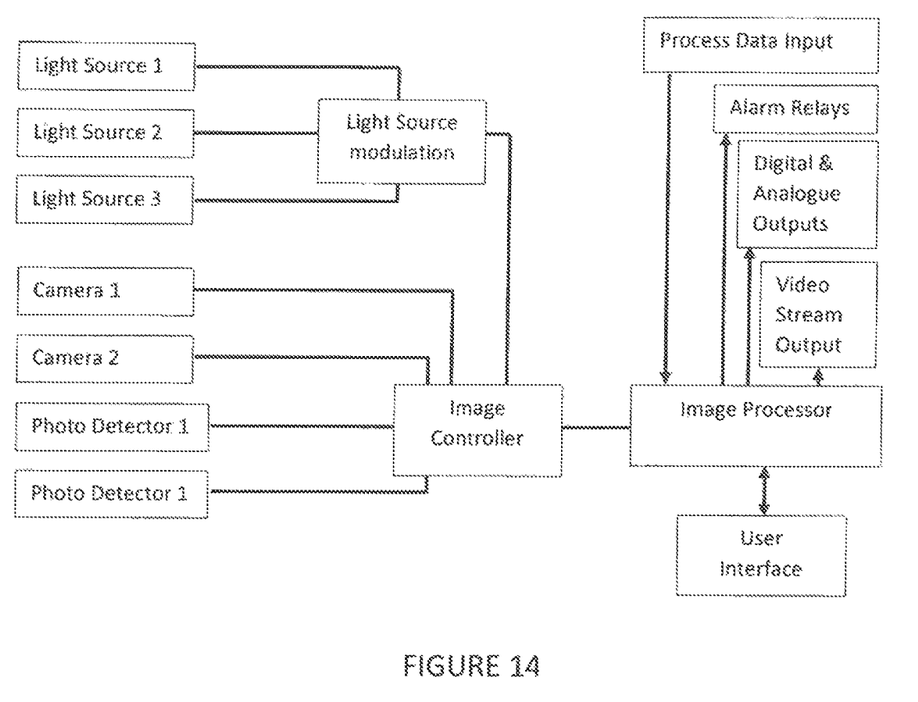

FIG. 14 illustrates a system using multiple light sources. One or more light sources may be used to illuminate the field of view, or part of the field of view, from different angles and/or wavelengths. One or more cameras or detectors may be used to collect data and images. The imaging controller can vary the frame rate of camera systems, and the modulation frequency of the illumination system from continuous to high frequency modulations. The image processing system will analyse the frames or images to determine the flow regime, and take the appropriate measurements from the images to determine the characteristics of the flow, for example liquid content, liquid width, liquid depth, liquid area, liquid hold up, flow regime, and flow rate.

By viewing pipeline activity as well as providing measurements for key parameters, it allows operators to understand (and believe) what is being reported by the alarm systems. The onset of different flow regimes changes due to many different variables. It is important to understand the flow regime as it varies the type of measurement required to define the flow rate. It is also an indication of different levels of liquid flow.

Combining measurements of liquid at the pipe wall and in aerosol means a better estimation of total liquid flow can be made.

An illumination and imaging system to automatically determine the presence, and quantify the volume and flow rate, of liquid within a high pressure gas pipeline. The system can automatically measure different liquid flow regimes within the fluid flow. Modulated illumination of a variety of collimated and polarised light sources can aid the recognition and measurement of fluid flow.

The flow regime of liquid flows within large diameter pipelines depends on many factors and is difficult to accurately determine through Computational Flow Dynamics modelling (CFD). Most test flow loops to date are 2" or 3" or, les commonly 8" diameter pipes, and modelling is used to determine the flow regime in larger diameter pipes, and with liquids that have different densities and viscosities. The accuracy of these models in 12" diameter pipes and larger, is questionable. The use of visual data produced by this system can quantify liquid flow, and may be used to aid CFD models, or be used by operators, gas purchasers and sellers to determine the quality of the fluid at custody transfer points in order to establish its safety, and its suitability for entry into a pipeline network.

The invention claimed is:

1. An apparatus for detecting the presence of liquid in a high pressure gas pipeline, comprising:
   at least one sight glass, providing an aperture into the inside of the pipeline;
   one or more light sources;
   at least one light sensor, for receiving and sensing reflected light from the inside of the pipeline through the sight glass; and
   a processor, for automatically detecting the presence of a liquid based on the sensed reflected light
   characterised in that said light sensor is at least one imaging device for capturing images of the inside of the pipeline through said sight glass, said images comprising image data, and wherein the processor automatically detects the presence of a liquid based on characteristics of the captured images, and wherein the image data is associated with metadata;
   wherein the apparatus further comprises an illumination system for illuminating the inside of the gas pipeline within the field of view of the light sensor, and wherein the illumination system illuminates the inside of the gas pipeline with a combination of shaped and focused beams comprising one or more of spots, lines, grids or other patterns.

2. An apparatus according to claim 1, wherein said sight glass is recessed away from the gas pipeline via a side pipe.

3. An apparatus according to claim 1, wherein the gas pipeline is a natural gas pipeline.

4. An apparatus according to claim 1, wherein said light sensor is operable to measure the amount of reflected light from the inside of the pipeline, and the processor is operable to detect the presence of liquid in the gas pipeline based on the measured amount of reflected light.

5. An apparatus according to claim 4, wherein the processor is operable to detect the presence of liquid in the gas pipeline based on the degree of variation in the measured amount of reflected light.

6. An apparatus according to claim 1, wherein the metadata defines one or more of the time, date and location of capture of the image, the temperature within the pipeline, the pressure, gas flow, the liquid flow, flow regime, hydrocarbon dewpoint, calorific value, wobbe index, water vapour content, water dewpoint, hydrogen sulphide content, carbon dioxide content, nitrogen content, oxygen content, mercury content, benzene content, arsenic content or historical data for process parameters and an area where users can add notes and comments regarding the data, process variables and relevant activities taking place that may influence the data.

7. An apparatus according to claim 1, wherein the processor is operable to determine a liquid flow regime within the gas pipeline based on characteristics of the captured image.

8. An apparatus according to claim 7, wherein the processor is operable to calculate one or both a flow rate and an amount of liquid within the gas pipeline based on the determined liquid flow regime.

9. An apparatus according to claim 7, wherein the processor is operable to calculate the gas flow rate based on the velocity of particles and liquid aerosols in the pipeline.

10. An apparatus according to claim 1, wherein the processor is operable to calculate the flow rate of liquid within the gas pipeline from a combination of the amount of liquid calculated to be present at the pipe wall, and the amount of liquid calculated to be entrained within the gas flow.

11. An apparatus according to claim 1, wherein the processor is operable to estimate the volume of liquid entrained within the gas flow by determining the size, volume and velocity of liquid droplets entrained in the gas flow.

12. An apparatus according to claim 1, wherein the liquid flow regimes which the processor is capable of distinguishing between comprise two or more of a distributed flow, a beaded flow, a smooth stratified flow, a wavy stratified flow, a partial annular flow, a full annular flow, a slugged flow and a bubble flow.

13. An apparatus according to claim 1, wherein the liquid flow regime is determined by the processor to be a distributed flow if separate stationary, or near stationary, droplets appear upon the pipe wall in the captured image, with no continuous stream of liquid being present on the pipe wall.

14. An apparatus according to claim 13, wherein if the liquid flow regime is determined to be a distributed flow, an amount of liquid in the pipe is estimated by determining the size and number of droplets present on the pipe wall within the image.

15. An apparatus according to claim 13, wherein if the liquid flow regime is determined to be a distributed flow, a flow rate of liquid is calculated by determining an change in an amount of liquid over time within the captured images, the amount of liquid being determined from the size and number of droplets present on the pipe wall within the image.

16. An apparatus according to claim 1, wherein the liquid flow regime is determined by the processor to be a beaded flow if separate moving droplets appear upon the pipe wall in the captured image, with no continuous stream of liquid being present on the pipe wall.

17. An apparatus according to claim 16, wherein if the liquid flow regime is determined to be a beaded flow, a flow rate of liquid is calculated by determining the size and velocity of the moving droplets.

18. An apparatus according to claim 1, wherein the liquid flow regime is determined by the processor to be a smooth stratified flow if a continuous and smooth stream of liquid is observed on the pipe wall.

19. An apparatus according to any one of claims 11, wherein a continuous stream of liquid is determined to be present in the image using edge detection.

20. An apparatus according to claim 18, wherein if the liquid flow type is determined to be a smooth stratified flow, the volume of liquid in the pipe is calculated in dependence on the width of the stream of liquid within the image and the known geometry of the gas pipeline.

21. An apparatus according to claim 20, wherein the width of the stream of liquid is determined by comparing the width of the stream within the image with known reference points within the image.

22. An apparatus according to claim 18, wherein an optical system and processor are operable to detect a flow velocity at the surface of the liquid at different positions across the width of the liquid stream, and to calculate the volumetric flow of the liquid stream based on a flow velocity profile across the width of the stream.

23. An apparatus according to claim 1, wherein the liquid flow regime is determined by the processor to be a wavy stratified flow if a continuous stream of liquid is present on the pipe floor with periodic pulses of liquid detected on the surface which cause the width and/or depth of the stream of liquid in the image to vary.

24. An apparatus according to claim 23, wherein if the liquid flow regime is determined to be a wavy stratified flow, the volume of liquid in the pipe is calculated in dependence on the average width of the stream of liquid within the image, one or more of the size, frequency and duration of the pulses of liquid, and the known geometry of the gas pipeline.

25. An apparatus according to claim 1, wherein the liquid flow regime is determined by the processor to be part-annular or full-annular if a flow of liquid is detected in the image, but no edges can be observed within the field of view of the sensor.

26. An apparatus according to claim 25, wherein the processor is operable to distinguish between a part-annular and full-annular flow regime using a detected flow velocity profile within the field of view of the imaging device.

27. An apparatus according to claim 21, wherein if the liquid flow type is determined by the processor to be full-annular, the volume of liquid in the pipe is calculated by estimating the depth of liquid at the bottom of the pipe and the depth of liquid at one or more other points on the pipe wall circumference to calculate the average film depth of liquid on the pipe wall and hence the volume of liquid. Liquid flow may be determined by determination of surface flow across the observed field of view.

28. An apparatus according to claim 1, wherein said sight glass is recessed from the gas pipeline within a side pipe, and wherein the liquid flow regime is determined by the processor to be slugged flow if liquid pulses are observed by the imaging device to extend into the side pipe.

29. An apparatus according to claim 28, wherein the processor is operable to estimate the average flow rate from the frequency and duration of the pulses.

30. An apparatus according to claim 1, wherein the liquid flow regime is determined by the processor to be bubble flow if bubbles of gas are observed within a transparent or partly transparent liquid.

31. An apparatus according to claim 30, wherein if the liquid flow regime is determined by the processor to be a bubble flow, the volume of liquid or gas in the pipe is calculated from the known pipeline geometry and the average volume of the observed bubbles within the field of view.

32. An apparatus according to claim 1, wherein the processor is operable to detect heat haze from a distortion or obscuration of one or more known reference features within the field of view of the imaging device, and to compensate for the heat haze in the analysis of captured images.

33. An apparatus according to claim 1, wherein the processor is operable to detect heat haze from a distortion of one or more illumination patterns projected into the pipeline, and to compensate for the heat haze in the analysis of captured images.

34. An apparatus according to claim 1, wherein the illumination system is monochromatic.

35. An apparatus according to claim 1, wherein the illumination system illuminates the inside of the gas pipeline using multiple wavelengths selected from visible light, infra-red, ultra violet and terahertz.

36. An apparatus according to claim 1, wherein the beams are static or moving.

37. An apparatus according to claim 1, wherein the illumination system projects collimated or uncollimated light into the gas pipeline.

38. An apparatus according to claim 1, wherein an illumination source of the illumination system is in line with the light sensor.

39. An apparatus according to claim 1, wherein an illumination source of the illumination system is offset from the light sensor.

40. An apparatus according to claim 1, wherein the illumination system projects a pattern of illumination outside of the field of view of the light sensor.

41. An apparatus according to claim 1, wherein the illumination system illuminates the inside of the pipe a plurality of times within an image capture period of the imaging device.

42. An apparatus according to claim 41, wherein the velocity of particles or droplets is calculated from the distance travelled by a particle or droplet between successive illuminations or image frames of the inside of the pipeline.

43. An apparatus according to claim 1, wherein the velocity of particles, bubbles or droplets is calculated from the distance travelled by a particle, bubble or droplet between successive imaging periods of the imaging device.

44. An apparatus according to claim 1, wherein the processor is operable to detect the presence of a liquid in dependence on the file size of images or sequences of images captured by the imaging device.

45. An apparatus according to claim 5, wherein the processor is operable to detect the presence of a liquid in dependence on the total or average intensity of pixel values in the captured image.

46. An apparatus according to claim 1, the apparatus further comprising a lens.

47. An apparatus according to claim 46, the lens comprising a liquid lens.

48. An apparatus according to claim 46, the lens comprising a membrane lens.

49. An apparatus according to claim 1, wherein the processor and the optical system are operable to detect liquids via Doppler speckle contrast imaging.

50. An apparatus according to claim 1, wherein the processor and the optical system are operable to detect liquids via scanning LIDAR.

* * * * *